US012708761B2

(12) United States Patent
Valvano et al.

(10) Patent No.: US 12,708,761 B2

(45) **Date of Patent: *Aug. 18, 2026**

(54) METHOD AND APPARATUS FOR ASSISTING A HEART

(71) Applicants: Jonathan W. Valvano, Austin, TX (US); John Porterfield, Austin, TX (US); Clay Heighten, Dallas, TX (US); Anil Kottam, Cedar Park, TX (US); Marc David Feldman, San Antonio, TX (US); Aleksandra Borisovna Gruslova, San Antonio, TX (US); Drew R. Nolen, San Antonio, TX (US)

(72) Inventors: Jonathan W. Valvano, Austin, TX (US); John Porterfield, Austin, TX (US); Clay Heighten, Dallas, TX (US); Anil Kottam, Cedar Park, TX (US); Marc David Feldman, San Antonio, TX (US); Aleksandra Borisovna Gruslova, San Antonio, TX (US); Drew R. Nolen, San Antonio, TX (US)

(73) Assignees: Board of Regents, The University of Texas System, Sandy Springs, GA (US); CardioVol, LLC, Dallas, TX (US)

(*) Notice: Subject to any disclaimer, the term of this patent is extended or adjusted under 35 U.S.C. 154(b) by 18 days.

This patent is subject to a terminal disclaimer.

(21) Appl. No.: 18/584,877

(22) Filed: Feb. 22, 2024

(65) Prior Publication Data

US 2024/0198081 A1 Jun. 20, 2024

Related U.S. Application Data

(63) Continuation of application No. 17/238,181, filed on Apr. 22, 2021, now Pat. No. 11,911,602.

(51) Int. Cl.
*A61M 60/515* (2021.01)
*A61M 60/13* (2021.01)
(Continued)

(52) U.S. Cl.
CPC .......... *A61M 60/515* (2021.01); *A61M 60/13* (2021.01); *A61M 60/165* (2021.01);
(Continued)

(58) Field of Classification Search
CPC .............. A61M 60/867; A61M 60/237; A61M 60/531; A61M 60/515
See application file for complete search history.

(56) References Cited

U.S. PATENT DOCUMENTS 7,925,335 B2 4/2011 Feldman et al.
9,295,404 B2 3/2016 Valvano et al.
(Continued)

OTHER PUBLICATIONS

Haines, et al., Validation of a defribrillation lead ventricular volume measurement compared to the three-dimensional echocardiography. Heart Rhythm. Oct. 2017; 14(10):1515-22.
(Continued)

*Primary Examiner* — Jennifer Pitrak McDonald
*Assistant Examiner* — Jennifer L Ghand
(74) *Attorney, Agent, or Firm* — Ansel M. Schwartz

(57) ABSTRACT

An apparatus for a heart of a patient having a cardiac assist device adapted to be implanted into the patient to assist the heart with pumping blood. The apparatus has a sensor adapted to be implanted into the patient. The sensor in communication with the cardiac assist device and the heart which measures native volume of the heart. Alternatively, the sensor monitors the heart based on admittance while the cardiac assist device. Alternatively, the sensor monitors the heart based on impedance.

7 Claims, 7 Drawing Sheets

(51) Int. Cl.

| | |
|---|---|
| ***A61M 60/165*** | (2021.01) |
| ***A61M 60/237*** | (2021.01) |
| ***A61M 60/523*** | (2021.01) |
| ***A61M 60/531*** | (2021.01) |
| ***A61M 60/816*** | (2021.01) |
| ***A61M 60/867*** | (2021.01) |
| ***G05B 19/04*** | (2006.01) |
| ***G16H 20/30*** | (2018.01) |
| ***G16H 40/63*** | (2018.01) |

(52) U.S. Cl.

CPC ........ *A61M 60/237* (2021.01); *A61M 60/523* (2021.01); *A61M 60/531* (2021.01); *A61M 60/816* (2021.01); *A61M 60/867* (2021.01); *G05B 19/041* (2013.01); *G16H 20/30* (2018.01); *G16H 40/63* (2018.01); *A61M 2205/3317* (2013.01); *G05B 2219/25257* (2013.01)

(56) References Cited

U.S. PATENT DOCUMENTS

| | | | | |
|---|---|---|---|---|
| 9,820,673 | B2 | 11/2017 | Feldman et al. | |
| 10,420,952 | B2 | 9/2019 | Feldman et al. | |
| 11,911,602 | B2 * | 2/2024 | Valvano | G05B 19/041 |
| 11,918,799 | B2 * | 3/2024 | Porterfield | A61M 60/139 |
| 11,931,563 | B2 * | 3/2024 | Porterfield | A61M 60/13 |
| 2008/0045779 | A1 * | 2/2008 | Rinaldi | A61M 60/569 600/16 |
| 2009/0143651 | A1 | 6/2009 | Kallback et al. | |
| 2015/0306290 | A1 * | 10/2015 | Rosenberg | A61B 5/0215 600/16 |
| 2019/0298997 | A1 * | 10/2019 | Valvano | G16H 40/63 |
| 2021/0346675 | A1 * | 11/2021 | Schlebusch | A61M 60/13 |
| 2022/0105339 | A1 | 4/2022 | Nix et al. | |
| 2022/0339428 | A1 | 10/2022 | Porterfield et al. | |

OTHER PUBLICATIONS

Larson, et al. Admittance to detect alterations in left ventricular stroke volume. Heart Rhythm. Jun. 27, 2014; 11(11):2075-83.
Agarwal, et al. Temporal Trends in Hospitalization for Acute Decompensated Heart Failure in the United States, 1998-2011. Am J Epidemiol. Mar. 1, 2016; 183(5):462-70.
Stretch, et al. National trends in the utilization of short-term mechanical circulatory support: incidence, outcomes, and . . . J Am Coll Cardiol. Oct. 7, 2014;64(14):1407-15.
Felker, et al., Heart Failure Clinical Research Network Investigators. Loop diuretics . . . Circulation: Heart Failure. American Heart Association, Inc.; Jan. 2009;2(1):56-62.
Mandawat, et al. Percutaneous Mechanical Circulatory Support Devices . . . Circ Cardiovasc Interv. American Heart Association, Inc.; May 2017; 10(5):e004337.
Burkhoff, et al. The science behind percutaneous hemodynamic support: . . . Catheter Cardiovasc Interv. Nov. 1, 2012;80(5):816-29.
Fincke, et al. Cardiac power is the strongest hemodynamic correlate of mortality in cardiogenic shock: . . . J Am Coll Cardiol. Jul. 21, 2004;44(2):340-8.
Torgersen, et al. Hemodynamic variables and mortality in cardiogenic shock: a retrospective cohort study. Crit Care. 2009;13(5):R157.
Mendoza, et al., Cardiac power output predicts mortality across a broad spectrum of patients with acute cardiac disease. American Heart Journal. Mar. 2007;153(3):366-70.
Uriel, et al., Development of a novel echocardiography ramp test for speed optimization and diagnosis of device thrombosis . . . J Am Coll Cardiol. Oct. 30, 2012;60(18):1764-75.
Uriel, et al., Left Ventricular Decompression During Speed Optimization Ramps in Patients Supported by Continuous-Flow Left . . . J Card Fail. Oct. 2015;21(10):785-91.
Trevino, et al. Validation of a new micro-manometer pressure sensor for cardiovascular measurements in mice. Biomed Instrum Technol. 2010;44(1):75-83.
Raghavan, et al. A bio-telemetric device for measurement of left ventricular pressure-volume loops using the admittance technique . . . Physiol Meas. Jun. 2011;32(6):701-15.
Larson, et al., Analysis of the spatial sensitivity of conductance/admittance catheter ventricular volume estimation. IEEE Trans Biomed Eng. Aug. 2013;60(8):2316-24.
Porterfield, et al. Dynamic correction for parallel conductance, GP, and gain factor, . . . J Appl Physiol. American Physiological Society Bethesda, MD; Dec. 2009;107(6):1693-703.
Holt, et al., A Real-Time Hemodynamic ICD Measurement: Evaluation in Chronically Implanted Canines . . . , J Am Coll Cardiol EP, vol. 5, No. 6, pp. 742-743, Jun. 2019 PMID: 31221363.
Porterfield, et al., Left ventricular epicardial admittance measurement for detection of acute LV dilation. J Appl Physiol. Mar. 2011;110(3):799-806.
Kottam, et al., Real time pressure-vol. loops in mice using complex admittance: measurement and implications. Conf Proc IEEE Eng Med Biol Soc. IEEE; 2006;1:4336-9.
Wei, et al., Volume catheter parallel conductance varies between end-systole and end-diastole. IEEE Trans Biomed Eng. Aug. 2007;54(8):1480-9.
Gabriel, et al., The dielectric properties of biological tissues: III. Parametric models for the dielectric spectrum of tissues. Phys Med Biol. Nov. 1996;41(11):2271-93.

* cited by examiner

METHOD AND APPARATUS FOR ASSISTING A HEART

CROSS-REFERENCE TO RELATED APPLICATIONS

This is a continuation of U.S. patent application Ser. No. 17/238,181 filed Apr. 22, 2021, now U.S. Pat. No. 11,911,602, incorporated by reference herein.

FIELD OF THE INVENTION

The present invention is related to measuring native volume of a heart of a patient having a cardiac assist device. Volume per time is flow, and typically defined as cardiac output (CO). The term, Native Flow, is not a standard term, but describes the difference between diastolic and systolic volumes as contributed by the contraction of the myocardium itself. The Native Cardiac Output is Native Volume times heart rate. In a patient without a cardiac assist device, Native CO is equal to total CO, and native volume is equal to stroke volume. However, in a patient with a pump, total CO=native CO+pump CO. (As used herein, references to the "present invention" or "invention" relate to exemplary embodiments and not necessarily to every embodiment encompassed by the appended claims.) More specifically, the present invention is related to monitoring a heart of a patient having a cardiac assist device with admittance or impedance.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Cardiomyopathy is a disease of the heart muscle that can lead to cardiogenic shock, a life-threatening condition in which the heart is unable to pump enough blood to support the body's vital organs. In the U.S. alone, cardiomyopathy causes 1.8 million hospitalizations per year and carries a 30% one-year mortality rate after hospital admission (3). Cardiomyopathy has annual Medicare costs of approximately $20 billion (4) and is the number one cause of hospitalizations and length of stay in patients greater than 65 years old (5). The incidence of cardiogenic shock is increasing, with a >2× increase in the number of cardiomyopathy discharges complicated by cardiogenic shock, from 2004-2014 (6). Cardiogenic shock occurs because the weakened heart suddenly cannot pump enough blood to the rest of the body to sustain it. In these cases, a short-term mechanical circulatory support (MCS) device can be placed in the heart to help maintain high forward blood flow while resting (mechanically unloading) the failing heart. These MCS devices are pumps that continuously draw blood from the left ventricle through an inlet port and expel the blood into the ascending aorta. The MCS can be inserted via a standard catheterization procedure through the femoral artery, into the ascending aorta, across the aortic valve, and into the left ventricle (FIG. 1). Once proper placement has been confirmed, the speed of the pump is set depending upon patient condition.

The ability of MCS devices to maintain peripheral perfusion while mechanically unloading the heart has the potential to improve mortality across at least three large groups of patients (7): 1. high risk percutaneous coronary intervention (PCI), 2. acute myocardial infarction (MI) with or without cardiogenic shock, and 3. acute decompensated heart failure.

While the first category of high-risk PCI is an elective surgery and is typically performed over a surgical (short) period, for the last two categories, MCS devices are implanted for up to 6 days as a bridge-to-recovery or bridge-to-decision for a more long-term ventricular assist implant. In these patients, indwelling time is longer, and bridging to recovery is not guaranteed.

This is a vast improvement over current practice, whereby a static pump flow is set for the MCS at implant and does not change until the physician decides to initiate the judgement-based and arduous device removal weaning process. There are several risks to the patient in prolonging the initiation of this device removal process including longer recovery time and sepsis.

BRIEF SUMMARY OF THE INVENTION

The present invention pertains to an apparatus for a heart of a patient. The apparatus comprises a cardiac assist device adapted to be implanted into the patient to assist the heart with pumping blood. The apparatus comprises one or more sensors adapted to be implanted into the patient. The sensor(s) in communication with the cardiac assist device and the heart which measures native volume of the heart. The apparatus may be used with a patient during recovery or in high risk, such as percutaneous coronary, intervention.

The present invention pertains to an apparatus for a heart of a patient. The apparatus comprises a cardiac assist device adapted to be implanted into the patient to assist the heart with pumping blood. The apparatus comprises one or more sensors adapted to be implanted into the patient. The sensor(s) in communication with the cardiac assist device and the heart which monitors the heart based on admittance while the cardiac assist device is in operation.

The present invention pertains to an apparatus for a heart of a patient. The apparatus comprises a cardiac assist device adapted to be implanted into the patient to assist the heart with pumping blood. The apparatus comprises one or more sensors adapted to be implanted into the patient. The sensor(s) in communication with the cardiac assist device and the heart which monitors the heart based on impedance while the cardiac assist device is in operation.

The present invention pertains to a method for treating a heart of a patient. The method comprises the steps of pumping blood of the patient with a cardiac assist device implanted into the patient. There is the step of measuring native volume of the heart with one or more sensors implanted into the patient, the sensor(s) in communication with the cardiac assist device and the heart.

The present invention pertains to apparatus for a heart of a patient. The apparatus comprises a cardiac assist device adapted to be implanted into the patient to assist the heart with pumping blood. The apparatus comprises one or more sensors adapted to be implanted into the patient. The sensor(s) producing a source signal. The sensor(s) in communication with the cardiac assist device and the heart which monitors the heart with the source signal. The sensor dynamically shifting the source signal to avoid noise from the pump or other sources.

The present invention pertains to a method for assisting a heart of a patient. The method comprises the steps of producing a source signal by one or more sensors implanted in the patient. The sensor(s) in communication with a cardiac assist device implanted into the patient to assist the heart with pumping blood and the heart. There is the step of monitoring the heart by the sensor with the source signal. There is the step of the sensor dynamically shifting the source signal to avoid noise from the pump or other sources.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 1:
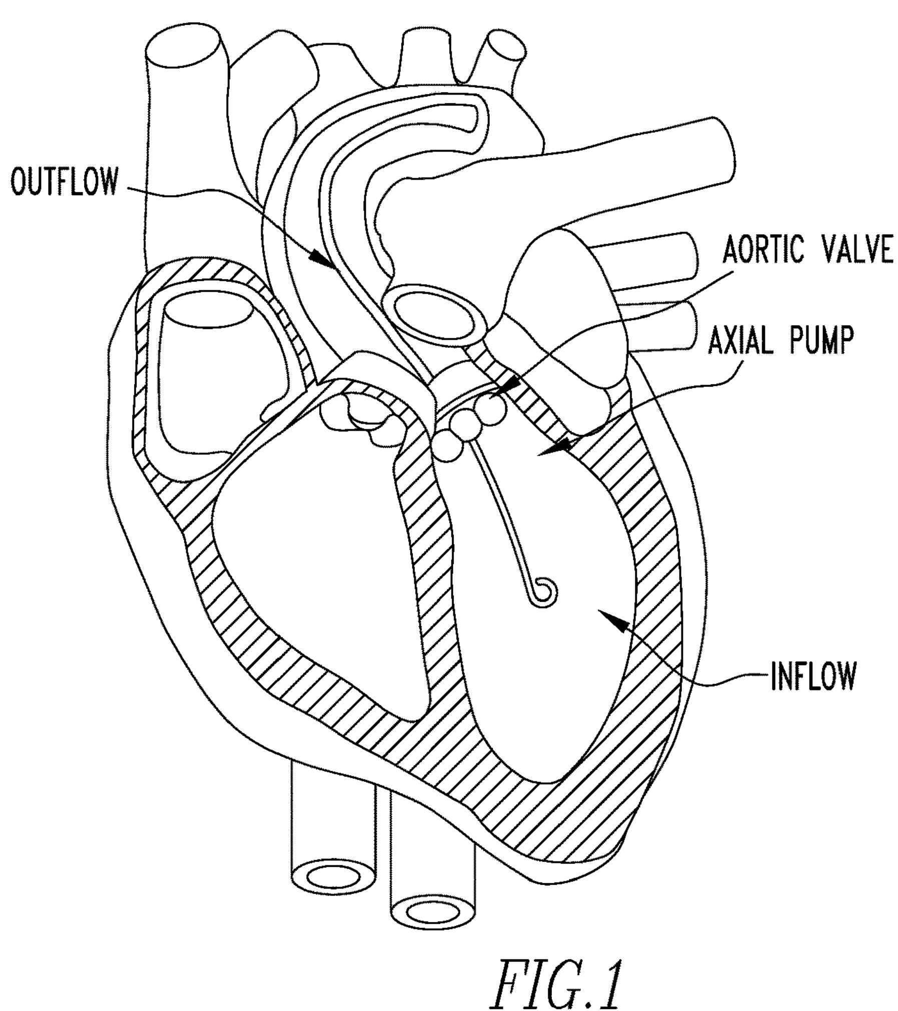
FIG. 1 shows the claimed invention in conjunction with the heart.
Figure 2:
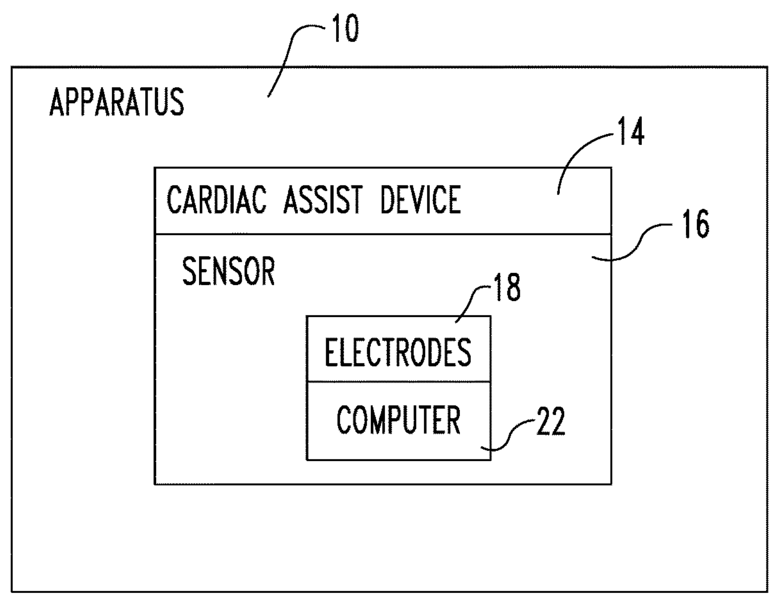
FIG. 2 is a block diagram of the claimed invention.
Figure 3:
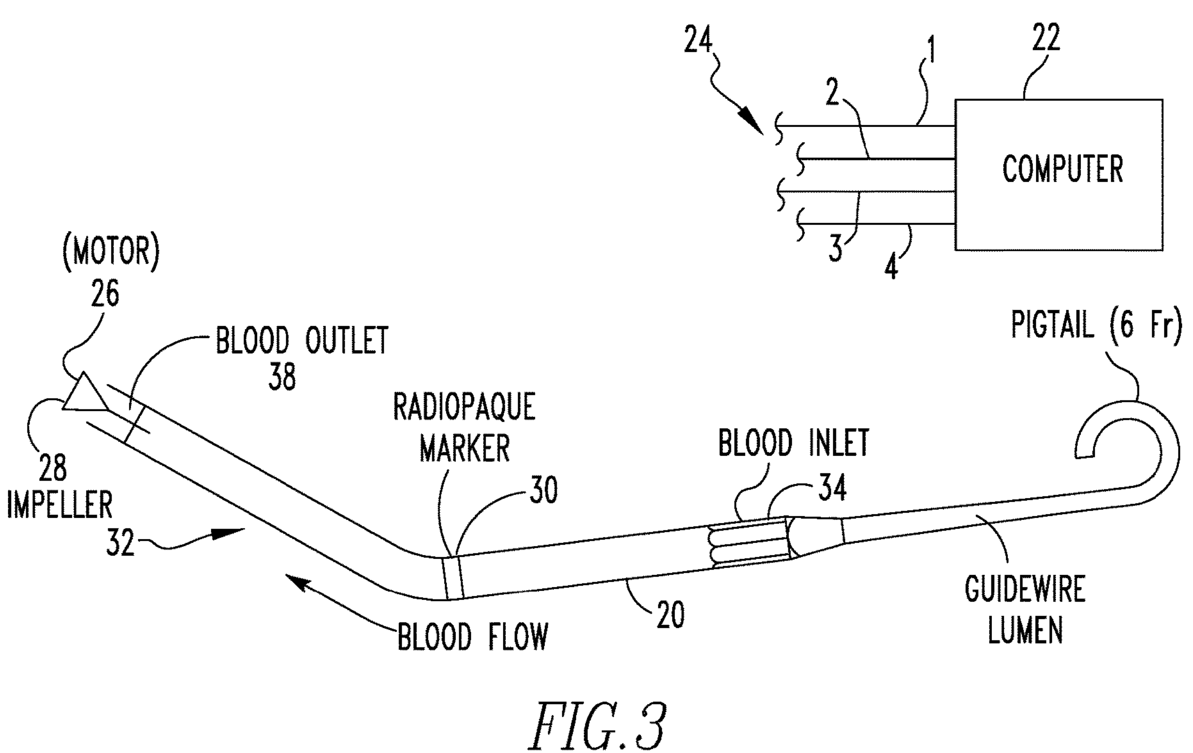
FIG. 3 shows the claimed invention.

Referring now to the drawings wherein like reference numerals refer to similar or identical parts throughout the several views, and more specifically to FIGS. 1, 2 and 3 thereof, there is shown an apparatus 10 for a heart 12 of a patient. The apparatus 10 comprises a cardiac assist device 14 adapted to be implanted into the patient to assist the heart 12 with pumping blood. The apparatus 10 comprises one or more sensors 16 adapted to be implanted into the patient. The sensor(s) 16 in communication with the cardiac assist device 14 and the heart 12 which measures native volume and pressure of the heart 12. The apparatus 10 may be used with a patient during recovery or in high-risk percutaneous coronary intervention.

The sensor 16 may include electrodes 18 directly attached to the cardiac assist device 14 that produce signals which are used to measure the native volume and pressure of the heart 12. The cardiac assist device 14 may have a shaft 20 that is adapted to be positioned in the heart 12, and the electrodes 18 are in contact with the shaft 20 that is positioned in the heart 12 chamber. The electrodes 18 should be in the chamber of interest for the sensor 16 to work properly. If the electrodes 18 are not in the chamber of interest, the sensor 16 most likely will not work.

The sensor 16 may include a computer 22 for data acquisition and analysis of the signals. The computer 22 is in communication with the electrodes 18. The computer 22 may provide electrical currents to the electrodes 18 and may measure corresponding voltages to make admittance-based measurements and analyze the admittance-based measurements to make real-time volume and pressure measurements of the heart 12. The sensor 16 may include wiring 24 that is in direct contact with the electrodes 18 and which extends to the computer 22 over which the electrical currents pass creating the corresponding voltages. There may be a pressure sensor 51 adapted to be implanted into the patient. The pressure sensor 51 in communication with the cardiac assist device 14 and the heart and the computer 22 which monitors the left ventricular pressure while the cardiac assist device 14 is in operation. In addition, the pressure sensor with the computer may plot native pressure volume loops while the cardiac assist device is in operation, for instance, to measure the work done by the heart and its efficiency. A considerable amount of information on cardiac performance can be determined from the pressure vs. volume plot.

The cardiac assist device 14 may include a motor 26 and an impeller 28 disposed in the shaft 20 which is driven by the motor 26 to assist the heart 12 with pumping blood. The cardiac assist device 14 may have a marker 30 to guide proper placement of the cardiac assist device 14 in the heart 12. The electrodes 18 may be disposed on the shaft 20 of the device. Alternatively, the apparatus 10 may include a catheter having a shaft 20 disposed alongside the shaft 20 of the device and the electrodes 18 may be disposed alongside the shaft 20.

The cardiac assist device 14 may be a temporary mechanical circulatory support (MCS) device which is a catheter-mounted blood pump that draws blood from a left ventricle of the heart 12 through an inlet port 34 of the MCS 32 and expels blood into an ascending aorta 36 of the heart 12, thereby reducing some of the mechanical load on the heart 12 and promoting recovery. The pump may draw the blood intermittently in a pulsatile manner that mimics the natural pulsatile movement of the heart 12 or the pump may draw the blood from the left ventricle continuously. If the pump draws the blood intermittently, the timing of the intermittent action and the pulsing of the pump blood may be coordinated with the pumping motion of the heart 12. The native cardiac output (CO) and pressure measurements by the sensor 16 may provide a feedback signal to the MCS 32 to modulate flow/volume by the MCS 32 during treatment.

In contrast to having utility for weaning and treatment in a temporary MCS device that is catheter-mounted and connected to a mains powered external controller, a permanent implant battery-powered MCS device (often used for bridge-to-transplant rather than bridge-to-recovery), would benefit from a feedback signal to control pump speed in different scenarios. These include battery management, demand feedback, and long-term dysfunction diagnosis, for example, battery management is important in implanted devices, whether rechargeable or not, because patient's quality of life is typically tied to how unobtrusive the device is to the activities of everyday living. In general, the faster the pump flow, the more power is necessary to produce that flow. Total flow is the important metric to sustain in patients with an implantable MCS device, so having a high pump flow when the native output is high unnecessarily wastes battery life, directly leading to lower quality of life.

Demand feedback is typically unimportant in temporary MCS scenarios, because they are typically indicated for rescue, or high-risk situations (like high-risk PCI). In these emergent situations, the pump flow is typically set for as high as the patient will tolerate, because larger total flow for short periods is protective, while total flow that is slightly low can be extremely detrimental due to concomitant conditions. In long-term implant scenarios, the patient will exhibit a larger range of possible flow demand, for example, when exercising, for which a higher-than-normal pump flow is necessary. Other devices like demand pacers (https://www.biotronik.com/en-us/products/services/cls) measure and respond to this demand by using end systolic volume (the minimum volume sensed) as a surrogate for contractility, which is a marker for blood flow demand. This technique of demand measurement has the advantage of not being tied directly to activity, which could easily be measured using accelerometers. One example of non-activity related demand is changing pump flow to meet the demands on the body created by intense emotion (anger typically requires higher blood flows, and also increases contractility on a beat-to-beat basis, for example). Demand pacers can increase cardiac output by increasing heart rate, but a long term MCS device could directly modulate higher blood flow (stroke volume) instead.

Long-term dysfunction due to remodeling changes in the heart (usually marked by an increase in end-diastolic volume over time) are too long of a time scale to matter in temporary MCS devices. However, in completely implanted MCS devices, the native heart measurement can be used to detect worsening (or improving) heart failure status purely as a diagnostic.

The present invention pertains to an apparatus 10 for a heart 12 of a patient. The apparatus 10 comprises a cardiac assist device 14 adapted to be implanted into the patient to assist the heart 12 with pumping blood. The apparatus 10 comprises one or more sensors 16 adapted to be implanted into the patient. The sensor(s) 16 in communication with the cardiac assist device 14 and the heart 12 which monitors the heart 12 based on admittance while the cardiac assist device 14 is in operation.

The present invention pertains to an apparatus 10 for a heart 12 of a patient. The apparatus 10 comprises a cardiac assist device 14 adapted to be implanted into the patient to assist the heart 12 with pumping blood. The apparatus 10 comprises one or more sensors 16 adapted to be implanted into the patient. The sensor(s) 16 in communication with the cardiac assist device 14 and the heart 12 which monitors the heart 12 based on impedance while the cardiac assist device 14 is in operation.

The present invention pertains to a method for treating a heart 12 of a patient. The method comprises the steps of pumping blood of the patient with a cardiac assist device 14 implanted into the patient. There is the step of measuring native volume of the heart with one or more sensors 16 implanted into the patient. The sensor(s) 16 in communication with the cardiac assist device 14 and the heart 12. The method can also, or alternatively, use the sensor 16 and the cardiac assist device in the various embodiments described herein.

In the operation of the invention, a temporary MCS 32 device is a catheter-mounted blood pump, typically placed for less than 7 days in patients with cardiomyopathy and cardiogenic shock, that continuously draws blood from the left ventricle through an inlet port 34 of the MCS 32 and expels the blood into the ascending aorta 36, thereby reducing some of the mechanical load on the heart 12 and promoting recovery (hemodynamic support). An MCS 32 is unlike other more permanently placed pumping devices, because it is placed in the patient using a standard catheterization procedure (without piercing the heart 12). This technique is preferable for use as a bridge-to-recovery, because it can be easily removed. Once proper placement has been confirmed, the speed of the pump is set depending upon patient condition on a case-by-case basis, and treatment is deemed complete once the heart 12 has recovered and hemodynamics have returned to normal.

Initiating the device removal weaning process is based upon numerous factors, most importantly Cardiac Power Output (CPO=CO*Mean Atrial Pressure). During continuous use of an MCS 32 device, the total CO to the body comes from two components: total CO="native CO"+"device CO". "Native CO" is the amount of blood ejected from the ventricle by the recovering heart 12, and "device CO" is the amount of blood pumped by the MCS 32 device. Over time, the native CO from the heart 12 naturally rises, as it recovers slowly from decreased load, signaling improvement. Removal of the MCS 32 device requires "weaning" the patient from pump support by reducing pump speeds prior to removal. Optimal MCS 32 use would require reducing pump speed over an extended time as the native CO reaches near-normal levels, but in practice native CO is never measured during recovery, because it is clinically impractical to continuously measure CO using echocardiograms during the entire recovery period (could be days).

Ideally, an MCS 32 device would continuously measure real-time native CO, and then automatically adjust the pump speed to modify the device CO, while maintaining an overall total CO. This method would naturally wean the patient as he/she recovers as the native CO rises. The physician could monitor the native CO measurement and remove the MCS 32 device when appropriate. In Phase I, BSM proved that accurate measurements of real-time native CO are possible using an admittance-based Impella prototype ("Impella-CO") while operating within electromechanical pump noise. This was designed and demonstrated both on the bench, and in an animal model showing excellent agreement with multiple CO standards.

Figure 4:
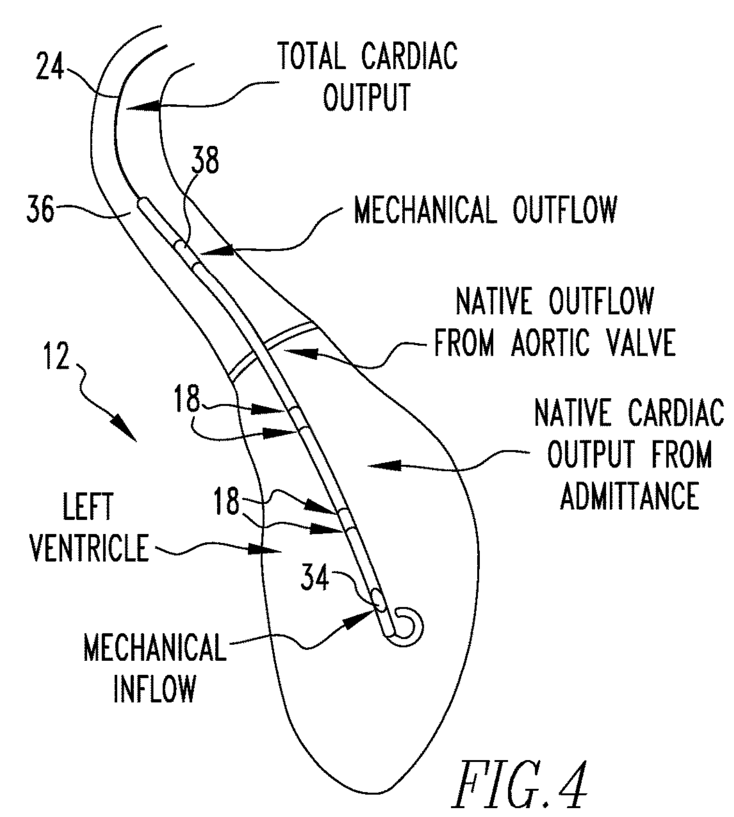
FIG. 4 shows the cardiac assist device and electrodes in conjunction with the heart.

Admittance measurement is blocked by electrical insulators like the pump body (made of plastics). It can only tell what the volume of the outside blood pool is, because the measurement relies on the flow of electricity being "admitted." Total CO is very easy to measure, and can be done using a number of different methods (Fick, Thermodilution, etc.). Native CO of the left ventricle can only be determined by imaging methods (directly visualizing the size of the pumping chamber, the LV), and Admittance. As shown in FIGS. 1 and 4, the outlet port 38 of the device is in the ascending aorta 36, outside of and downstream from the chamber of the heart 12. In this way blood from the outlet port 38 mixes with the native output of blood from the heart 12, downstream of where blood pumped solely by the heart 12 leaves the heart 12, so only the Native CO is measured by admittance. The blood inside the device is not measured because the pump body is made of plastic and shields the blood in the pump from being measured.

The pump typically does not directly measure the amount of flow going through it, and can only estimate its own flow (not usually measure it directly) by using the power delivered to/consumed by the pump as a surrogate for how hard the pump is working to pump blood (assuming the inlet and outlet remain unblocked).

Native Cardiac Output is the amount of forward blood flow that is due to the pumping action of the heart 12. To clarify, when there is no pump present, Cardiac Output is equal to Native Cardiac Output. When there is a pump present, the pump flow (the flow of blood through the pump)

in L/min is the pump output. Then, the total Cardiac Output is equal to the pump flow plus the Native Cardiac Output. Total CO=Pump CO+Native CO.

Cardiomyopathy is a disease of the heart 12 muscle that can lead to cardiogenic shock, a life-threatening condition in which the heart 12 is unable to pump enough blood to support the body's vital organs. In the U.S. alone, cardiomyopathy causes 1.8 million hospitalizations per year and carries a 30% one-year mortality rate after hospital admission (3). Cardiomyopathy has annual Medicare costs of approximately $20 billion (4) and is the number one cause of hospitalizations and length of stay in patients greater than 65 years old (5). The incidence of cardiogenic shock is increasing, with a >2× increase in the number of cardiomyopathy discharges complicated by cardiogenic shock, from 2004-2014 (6). Cardiogenic shock occurs because the weakened heart 12 suddenly cannot pump enough blood to the rest of the body to sustain it. In these cases, a short-term mechanical circulatory support (MCS) device can be placed in the heart 12 to help maintain high forward blood flow while resting (mechanically unloading) the failing heart 12. These MCS 32 devices are pumps that continuously draw blood from the left ventricle through an inlet port 34 and expel the blood into the ascending aorta 36. The MCS 32 can be inserted via a standard catheterization procedure through the femoral artery, into the ascending aorta 36, across the aortic valve, and into the left ventricle (FIG. 1). Once proper placement has been confirmed, the speed of the pump is set depending upon patient condition.

The ability of MCS 32 devices to maintain peripheral perfusion while mechanically unloading the heart 12 has the potential to improve mortality across at least three large groups of patients (7): 1. high risk percutaneous coronary intervention (PCI), 2. acute myocardial infarction (MI) with or without cardiogenic shock, and 3. acute decompensated heart failure.

While the first category of high-risk PCI is an elective surgery and is typically performed over a surgical (short) period, for the last two categories, MCS 32 devices are implanted for up to 6 days as a bridge-to-recovery or bridge-to-decision for a more long-term ventricular assist implant. In these patients, indwelling time is longer, and bridging to recovery is not guaranteed.

Figure 5:
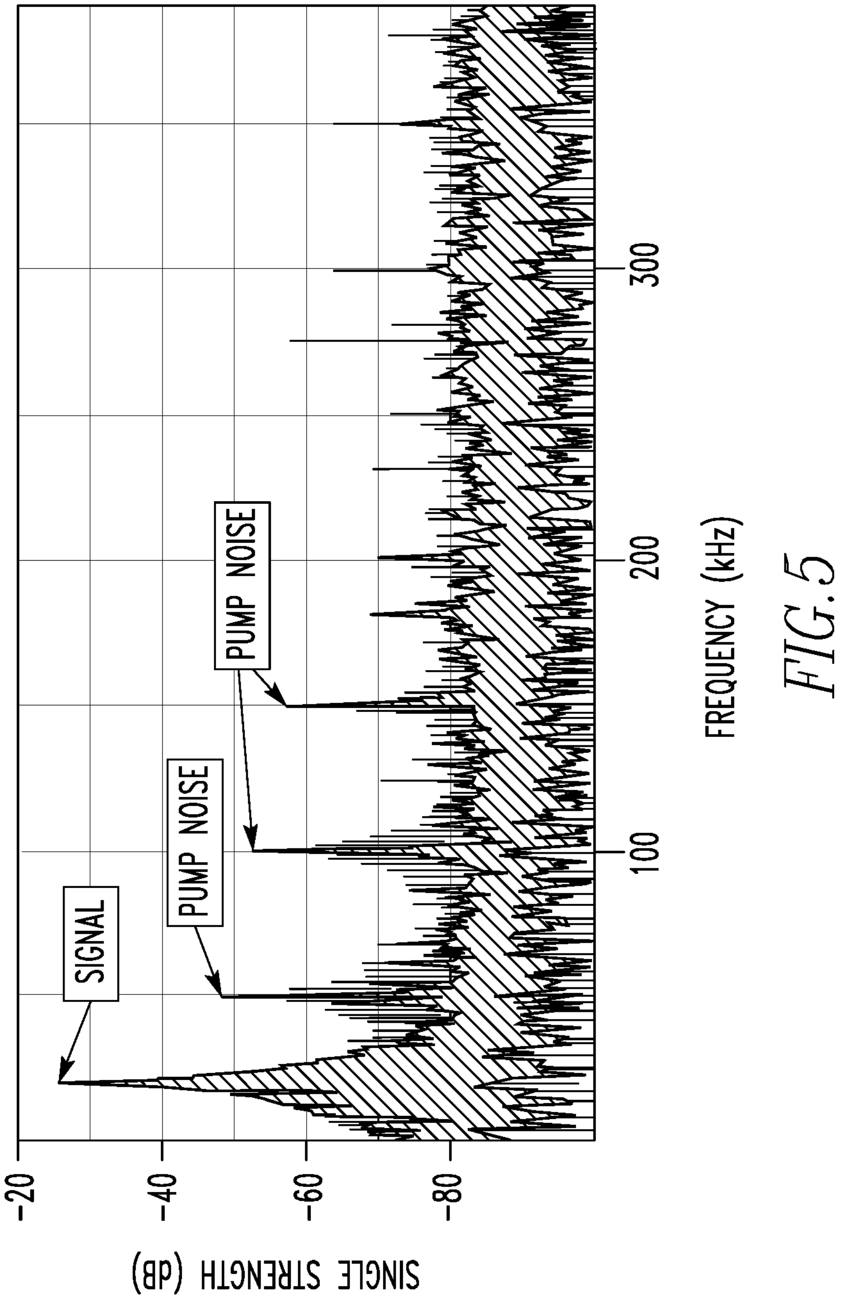
FIG. 5 shows a graph of frequency versus signal strength in regard to a simulated admittance measurement in a water bath with an Impella CP at minimum speed of 23,000 RPM.

Preliminary experiments were conducted on test MCS 32 devices provided by Abiomed to determine the initial noise spectrum (FIG. 5). The noise spectrum of the motor 26 vs. the "signal" (the 20 KHz waveform from CardioVol) was measured over all available pump speeds (0 to 46,000 rpm). It was determined that 1) pump noise is essentially the same regardless of pump speed, but has large spikes at 50, 100, and 150 kHz (this is good because Cardio Vol can operate at any frequency in the 1-100 KHz range, and is currently configured for 20 kHz) and 2) noise spectrum is dependent on the electrode geometry used (also good, because unlike traditional conductance, admittance utilizes only four electrodes 18 at a time, allowing flexibility in design that allows integration with existing devices like the MCS Impella).

FIG. 6 shows a black band located between the wiring 24 exit and the most proximal electrode that is radiopaque and used clinically to align with the aortic valve to guide proper placement. This design ensures that the surgeon will place all four electrodes 18 in the left ventricular heart 12 chamber.

Figures 6A, 6B, 6C, 7:
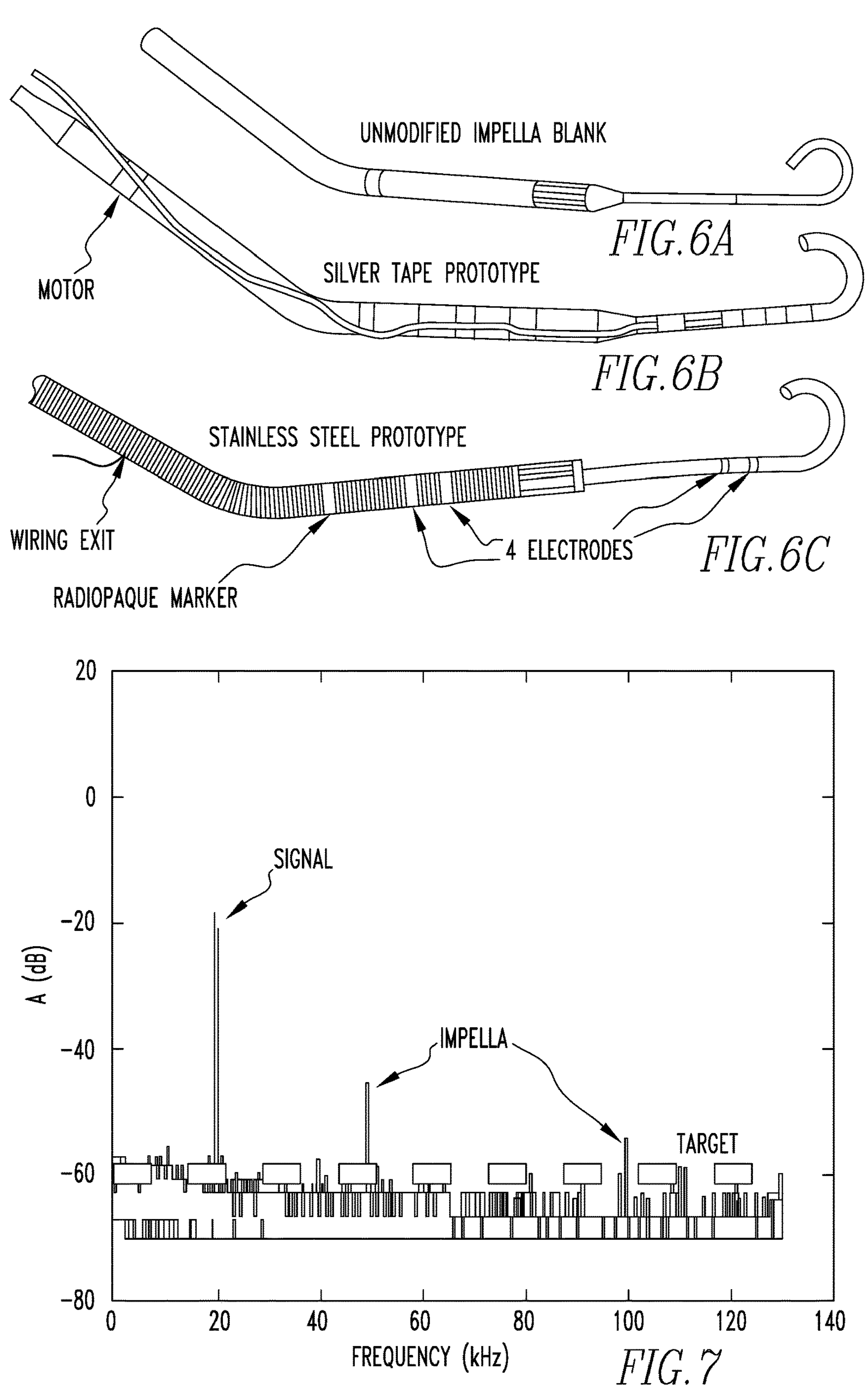
FIG. 6*a* shows an unmodified Impella device.
FIG. 6*b* shows a modified silver tape Impella device with electrodes.
FIG. 6*c* shows a modified stainless steel Impella device with four electrodes.
FIG. 7 shows a Fourier analysis of motor electromagnetic noise versus admittance signal for all 9 motor speeds.

Motor 26 noise quantification: Fourier frequency analysis of the motor 26 noise signal during pump operation was used to determine the optimal frequencies to use for the cardiac volume measurements. Volume calculations using admittance-based techniques allows for real-time measurement of both blood and muscle contributions by taking advantage of the differing electrical properties in the frequency range of interest. Within the frequency band of 1 kHz-100 kHz blood is purely resistive, but myocardium is both resistive and capacitive. Admittance measurements are performed in the complex Fourier plane, which allows measurement and separation of both the capacitive and resistive properties of the volume, allowing a pure measurement of blood volume to be extracted from the total signal. Because the measurement can be made at any frequency in the span, it is possible to pick a frequency that is uncorrupted by a known noise source, like that of the Abiomed Impella motor. As shown in 7, the excitation current signal used to make the Cardiac Output measurement (FIG. 7, Signal) is several orders of magnitude larger than the noise floor (FIG. 7, Noise floor Target). Note that the pump noise can be clearly seen at 50 khz, and at 100 kHz at all 9 pump speeds, and does not overlap with the measurement. It is clear from task 1 that any frequency at least 5 kHz away from DC, and not an integer multiple of 50 kHz could be utilized for the admittance-based volume measurement. 20 kHz is chosen for the prototype design to maximize signal to noise ratio while minimizing power and reducing the complexity of a higher frequency design. FIG. 7: In vitro testing with Pump at various levels showing low noise. Dynamic testing simulating a "heart beat" by squeezing the sides of a bottle while the pump is at P3, and P6. No filtering has taken place, and the raw admittance (volume) signal is unaffected by motor 26 noise.

Task 2: Modify the operating frequency and spatial electrode configuration of an admittance unit for maximum signal to noise ratio using information from task 1.

Admittance Unit Design: An instrument to measure admittance derived blood volume was designed to generate a constant amplitude current at an operating frequency of 20 kHz injected into the outer two electrodes 18 prototyped onto the Impella pump, and used to measure the resulting voltage from the inner two electrodes 18 as describe in task 1. Because the current is constant, the blood volume is proportional to the measured voltage from the inner two electrodes 18.

Figure 8:
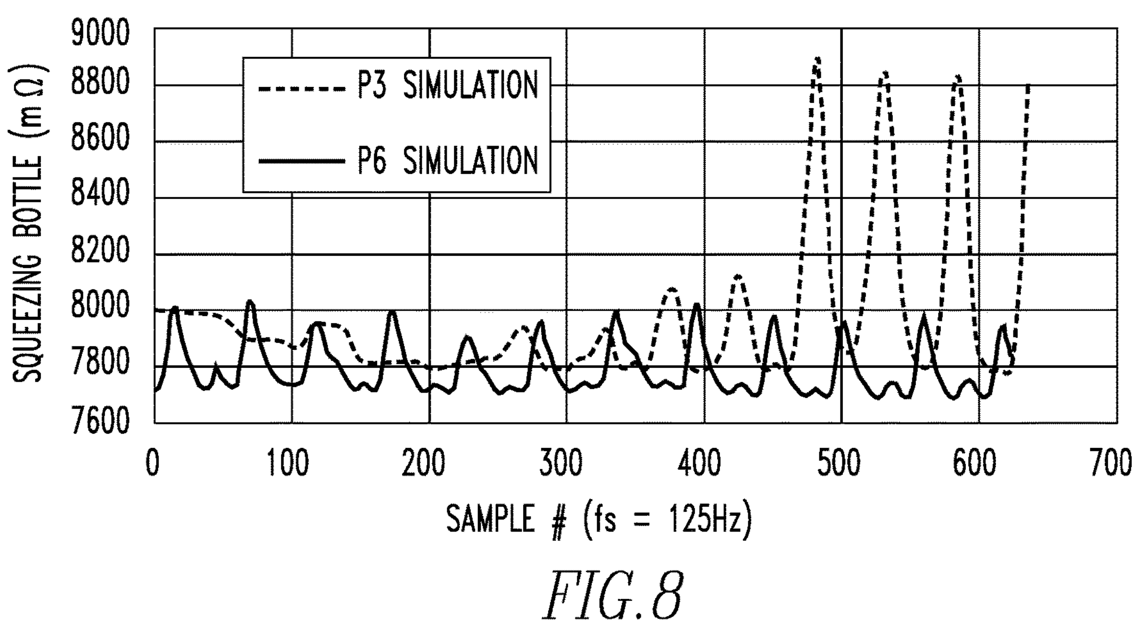
FIG. 8 shows in vitro testing with motor at various levels showing low noise.
Figure 9:
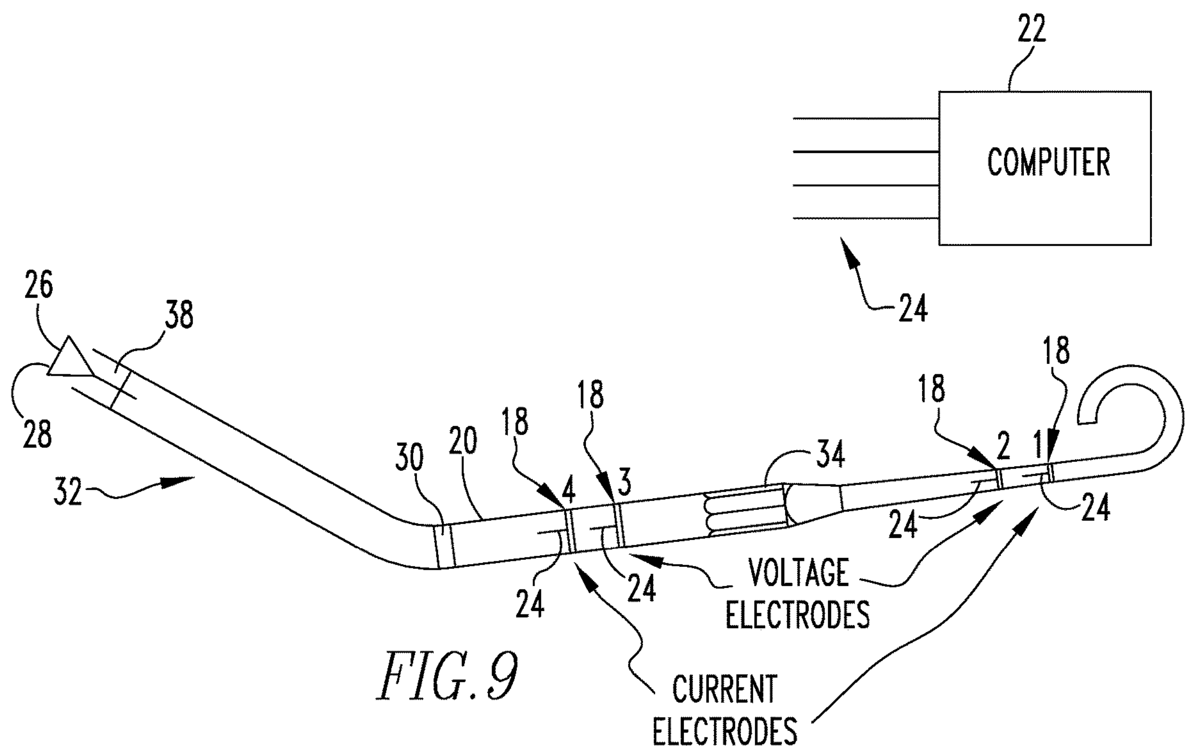
FIG. 9 shows the claimed invention.
Figure 10:
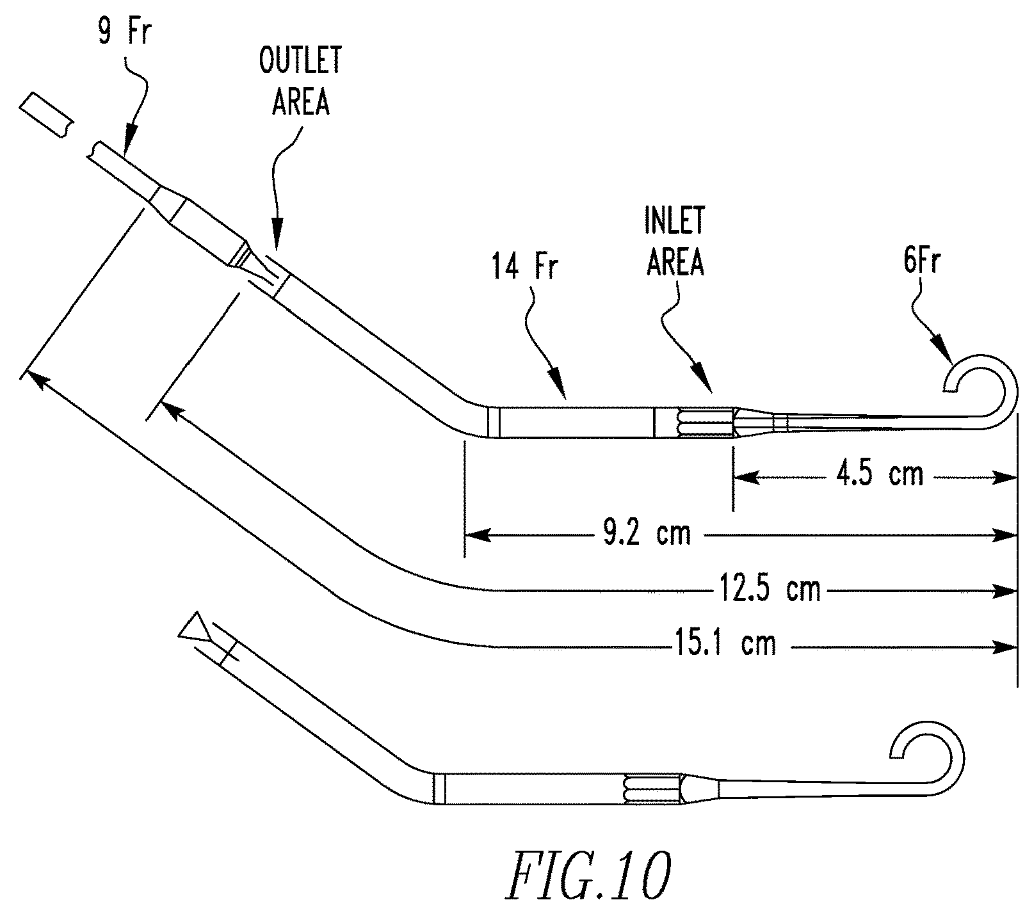
FIG. 10 shows the claimed invention.

In vitro testing: A bottle of saline with conductivity designed to mimic the conductivity of blood (s=8 mS/cm) was used to determine if the admittance measurement is sensitive to changing volumes in the presence of electrical pump noise, and because the bottle has flexible sides, it is possible to modulate the volume sensed near the Impella pump by repeatedly squeezing the bottle to simulate a beating heart 12. In this way, a time-varying signal is displayed on the GUI and recorded to examine signal quality (FIG. 8). The admittance instrument is shown to be highly responsive to changing volume in the bottle even in the presence of the pump operating at standard flow levels P3 and P6 (there are 9 pump speeds total, in addition to "off", so P3 and P6 represent middle values of speed). Note that when there is no simulated pumping, the motor 26 turning on does not change the value measured by the prototype Impella device, illustrating that the native CO is unaffected by motor 26 noise. The level of change caused by the pump in a stationary setup is less than 1 mΩ (milli-Ohm).

Signal to Noise Ratio (SNR) measurement: in vitro, SNR measurements are straightforward, and can be calculated using a discrete Fourier transform (DFT) on an oscilloscope, and an ideal signal which is derived from a continuous sine wave. However, in vivo, this measurement is not practical, given the added power required to maintain the continuous sine wave. Instead, a pulsed current excitation waveform is used to make extremely fast impedance measurements at 20 kHz, and calculate a Fast-Fourier Transform (FFT) in real time. This requires a modified SNR measurement approach for accuracy. In general, ReZ and ImZ are used to calculate the volume signal. Therefore, Signal (S) power can be calculated. The noise (T) can be calculated from all of the other bins of frequency in the FFT. In this way, an SNRa which varies from 0 to 1000 (1000 being a "perfect" no noise sine wave, and 0 being a lack of any discernable signal) can be calculated. Values above 900 are considered extremely low noise, and indicate a noise-free measurement in our in vivo measurements. The governing equations are shown below:

$$S = \mathrm{Re}Z^2 + \mathrm{Im}Z^2(V^2) \text{ at } 20 \text{ kHz}$$

$$T = \sum\nolimits_{non\ 20\ kHz\ bins} Sig - Avg$$

$$SNR_a = 1000 * S/T$$

Task 3: Measure native CO using admittance vs. standards in an animal model while simultaneously operating an MCS 32 device (Impella heart pump).

Goals: The goal for this preclinical evaluation was to measure CO using the admittance instrument connected to a prototype Abiomed Impella Mechanical Circulatory Support device and compare those measurements to standard clinical CO measurement methods. There is currently no universally accepted "gold standard" for CO measurement, and while every method has its weaknesses, our goal was to show good agreement with at least two of the current standards. Good agreement was defined as within-subject coefficient of variation (wCV)<20%, which is the agreement level that two expert echo readers show when reading the same set of echoes. 0% would indicate perfect agreement. wCV is mathematically defined as the standard deviation divided by the mean.

Protocol: N=3 pigs are instrumented with: 1) the modified Impella pump with CO measurement capability connected to the admittance unit, and 2) independently measured CO using a Swan Ganz catheter in the pulmonary artery capable of measuring 2A) CO via thermodilution continuous cardiac output, or CCO (Edwards Scientific), 2B) CO via bolus instantaneous cardiac output, or ICO (Edwards Scientific) and 2C) CO via myocardial oxygenation (Fick method). CO using 3) echocardiography with the aortic velocity time integral method, or aortic VTI at the level of the aorta are also measured. Measurements of CO were taken before the Impella pump was implanted, after the pump was implanted in the "off" state, and at each of the nine pump speeds (P1, P2, P3, P4, P5, P6, P7, P8, and P9). The protocol was discontinued if there was hemodynamic instability present, indicated by a "suction" alarm from the Impella. In all instances, "native heart" CO was calculated by taking the total CO measurement and subtracting the pump flow. The only exceptions were echo measurements (echo cannot measure the pump flow at the level of the aorta because the pump itself is opaque to sound waves), and admittance (admittance measures only the electrical properties of blood and myocardium outside the Impella because the catheter body is an electrical insulator opaque to electrical waves).

Results: In all three pigs, agreement with at least one of the standards (wCV≤16%) and in one of the pigs (Animal 2), wCV=9% for all 5 standards simultaneously were able to be shown, for all of the Impella pump speeds. Further, while there was no CO change planned in the protocol as a result of changing pump speed, the natural offloading of the heart 12 created by the Impella device shows a lower native CO for each progressively higher pump setting. This real phenomenon indicates not only that the Impella device offloads a failing heart 12 while maintaining forward CO and mean arterial pressure, but that it is possible to make this measurement in real-time using the prototype instrument developed.

Admittance vs. Conductance—There are three novel concepts that must be utilized to solve the problems preventing an Admittance measurement in situ with a generic noise source like a pump. 1) Traditional conductance catheters (including "dual frequency" devices) cannot determine accurate volumes because they all subtract a single value for parallel conductance. Using admittance-based technology solves these issues using a measurement of the capacitive nature of the myocardium, but both measurements are sensitive to noise from the motor 26, so frequency of operation must be redesigned. 2) The wires and electronics of an admittance-based catheter must be extremely small so as not to substantially increase the outer diameter of the MCS 32 device, which is 12 French in the case of the Abiomed Impella CP, (Danvers, MA) and 3) Electrode placement must be designed from scratch around the functional elements of the Impella device, which affects the field geometry.

General Considerations—In general, conductance measurements of volume are made by considering the chamber of interest and creating a custom catheter (a conductance catheter) that spans the area to make the most linear measurement of impedance possible. A measurement of admittance can be adapted for use on an arbitrary catheter, which is advantageous because many instruments are implanted either temporarily (like a percutaneous heart 12 pump or the cardiac assist device 14, see FIG. 1) or more permanently (like a cardiac implantable electronic device). These instruments often already have electrodes 18, microcontrollers, and signal processing that work in concert to achieve a goal like pacing the heart 12, or supporting a weak heart 12 by increasing forward flow. The adaptation of an admittance measurement to these existing resources can have diagnostic advantages at low additional cost, by carefully considering design tradeoffs to achieve a goal of low barrier to market entry, or reduction of contaminating noise. In this patent, it is discussed how to flexibly achieve both goals to combine a hemodynamic measurement with an existing heart 12 pump by taking advantage of two main ideas: 1) Working with non-ideal electrode locations, geometries, and inter-electrode spacing to linearize a measurement made in a non-linear region, and 2) using a frequency of measurement that avoids the noise of nearby, known interference.

Electrode Material—Electrodes 18 should be made of a biocompatible material, that is low resistance, like platinum or gold. The reasoning here is that the electrode itself should contribute as little as possible to the final measurement, making calibration less complicated.

Electrode Number—It is widely known that the electrode-electrolyte interface impedance that arises from putting a metal electrode in the presence of an electrolyte can change the measured total impedance. To protect against this, typically four electrodes (tetrapolar) 18 are necessary at a minimum, to reduce polarization effects. If numbered from the distal to the proximal end of a catheter as 1 (distal tip), 2, 3, 4 (most proximal electrode), typically electrodes 1 and 4 provide a function of current generation by injecting current, and 2 and 3 are used to measure the voltage arising from the current flowing through the electrolyte. Tetrapolar electrodes provide an advantage, because the design of a good constant current source does not change with electrode resistance change, ensuring that the admittance (current over voltage) does not change with fouling of electrodes 1 or 4.

Fouling is a change in resistivity that occurs due to a local change in the resistance of the electrode. Typically, this is caused by scar tissue formation, oxidation, or other change in the electrode/electrolyte impedance on the voltage electrode, either by changing the effective geometry, or the affecting the resistivity. This tetrapolar technique is used often in resistance/impedance measurements in non-medical fields.

If fewer electrodes 18 are desired or necessary (for example, if only three electrodes 18 are present, and used for another purpose, as when making an admittance measurement using a right ventricular implanted defibrillator lead, with a large shocking coil, ring, and tip conductor [1], [2]), then any electrode connected to both a current generation and voltage measurement should be the largest possible. This ensures that if electrode fouling occurs, it is likely that the change in total impedance will not affect the large percentage of the area. For example, $R=\rho*L/A$, and if the A is very large, then a change in resistivity of a small area $\Delta\rho/\Delta A$ will not affect the R by very much, even if Arho is large.

Electrode Spacing—If the outer two electrodes (1 and 4) are current generating, and the inner two electrodes (2 and 3) are voltage measuring, a naïve approach would be to equally space them. However, the sensitivity of a constant-current volume measurement is largest when the location of the current and voltage electrodes 18 is close together (that is, 1 and 2 are close together, 3 and 4 are close together), and far apart from the other pair (2 and 3 are far apart).

Additionally, any admittance change between current and voltage pairs (between 1 and 2, or between 3 and 4) will inversely affect the total admittance, a concept called "negative sensitivity".

As an example: consider a complex impedance measurement. If a high resistance, zero capacitance object enters between electrodes 2 and 3, then the real impedance measured will increase (because of the increased resistance to current flow, measured as a larger voltage on 2 and 3). If the same object enters between 1 and 2 instead, the real impedance will decrease (because the same voltage drop occurs between 2 and 3). This is the concept known as "negative sensitivity", and was first discussed by Larson et al [3]. In general, electrodes 1 and 2 (and also electrodes 3 and 4) should therefore be placed as close together as possible, given any limitations that must be worked around considering the geometry of the catheter shaft 20.

Ideal Electrode Geometry—The ideal physically realizable electrode for an admittance measurement would be a sphere, because it would allow for current output and voltage input from all directions simultaneously. However, to be disposed on a shaft 20 like a catheter, the closest that can be achieved is a ring. Typically, single electrodes are ring shaped, and about as long as their diameter. Using a ring shape makes the measurement independent of the rotational angle of the catheter. This allows the connection to the ring to be made within the catheter body (which is usually non-conducting) and keep the wiring 24 harness from affecting the impedance measurement. Additionally, it is not generally desirable to minimize the area of the electrode, because the impedance of the electrode itself should remain low to avoid affecting the measurement. This can be done by using a material with extremely low resistivity (usually at considerable cost if it remains biocompatible) or it can be done more easily by using a larger surface area. It has been found that a length about the size of the diameter is sufficient. In general, the ring size should be thin (the length L should be shorter than the diameter, d). Additionally, the cross-sectional area $\pi*d*L$ should be large enough that the resistance when placed in normal saline is <10 Ohms. The specific dimensions relate to the material properties of the electrode, and the geometry used (thin electrodes with $L<<d$ will have high resistance. Large d electrodes require a large catheter body, but will have a lower resistance). For the electrodes 18, the diameter should be the same as the catheter tubing diameter. The electrode diameter has a range of 2-5 mm and the electrode width to be 1-3 mm.

Wiring 24 Considerations—Connection of the electrodes 18 to the current source and voltage measurement is non-trivial, and in general, long, closely spaced wiring 24 creates a distributed capacitance that must be accounted for when calibrating. Wiring 24 must also be attached to the electrodes 18 in some way, ideally from the inside of the electrode ring. The catheter body is usually made of a non-conducting material, and if there is no necessary lumen, the wire routing can be made internal to the catheter, ensuring that the electrode surface area is not affected by the wire insulation. However, it is acceptable to route the wires outside of the catheter body, in particular when the lumen will need to be used, as in Embodiment 1 below. In these instances, the wiring 24 should be as thin as possible, bonded to the electrode in a way that uses minimal external surface area (so as not to affect the measurement). The wires themselves should be placed farther apart to minimize their effects on capacitance, and should not be coiled so as to minimize inductance effects.

Another potential advantage of having thin wires is that often times catheters only have lumens because they need to remain patent for the flow of a liquid. Thin wires can more easily avoid impeding this flow of liquid either physically, or avoid being used as a scaffold for clotting. Additionally, thinner wires are more easily capable of being built into the lumen walls to completely avoid these effects.

The wires leading to each of the four electrodes 18 create a capacitance between them. In general, it is possible to calibrate out if the wires stay the same distance from one another over the heartbeat. This is because changing distance between the wires over the heartbeat could be misrepresented as change in capacitance measured in myocardium.

Wire attachment is accomplished either by directly soldering the wire to the electrodes 18 themselves (typically from the inside of the lumen through a bored hole) or by using conductive epoxy solder paste through the same hole. It is possible to attach electrodes 18 to wires on the outside, but sensitivity to changes in the area of the solder joint may be changed by the electrical properties of the wire and attachment paste/solder. Electrical properties of the wire and attachment paste/solder are different depending on geometry, material, and material interface type, and these can all be either modeled using finite elements, or empirically measured in vitro using prepared saline that has the conductivity of blood.

The wires used to connect to the electrodes 18 will be 40 to 48 AWG to minimize any increase to the overall outer diameter of the pump. The wires should be insulated. Embedding the wires in the walls fixes their position with respect to one another, providing a constant resistive contribution. This will help with two factors: A) ease of calibration by keeping the effects of the wires constant, and B) it would allow keeping the outer diameter of the pump itself the same (which is an advantage surgically, because it means you do not need to increase the size of the delivery sheath or hole in the vessel).

Design for noise-band immunity—Admittance measurement in many different potential configurations has been discussed thoroughly in the past. When making these types of measurements in the presence of noise, analog or digital filtering can be employed to some success. However, when the noise band of interference is small, and does not span the entire optimal range of admittance measurement (10 kHz-100 kHz), [4], a change in current stimulation frequency and an aggressive bandpass filter on the voltage input can be used to avoid the noise entirely.

There are a few advantages to characterizing the aggressiveness of the noise in the Fourier domain. The closer a noisy band is to the frequency of the current source, the harder it is to use a filter, either analog or digital, to separate the signal from the noise. Using high Q analog filters can be expensive in parts, and high Q digital filters can be expensive computationally. Delays due to digital filtering at high Q can also pose problems. Changing the stimulation frequency of the current generation circuit only requires changes in the oscillator that is being used, allowing for cheaper and faster components to provide the signal processing necessary to make a complete measurement.

Improving SNR with dynamic SinDAC frequency—It is possible to choose a signal generation technique that will allow for small changes in the generated current frequency using only software, provided the signal generation is driven by a microcontroller clock or other oscillator that is sufficiently higher than the current generation frequency. In full designs such as those that use high Q analog filters on the voltage sampling section, only small changes in the current frequency generation are useful (less than 5% difference from the initial frequency), because the SNR of the returning voltage will suffer from degradation by the filter. Typically, the waveform is represented in microcontroller memory as an N-point waveform signal (a sine wave) reproduced point-by-point on a Digital to Analog Converter (a SinDAC) that has an output rate at or near the clock frequency. This limits the upper bounds of the SinDAC frequency output per the following equation:

$$\text{Sin}DAC\text{ frequency (Hz)} = \text{Clock Speed (Hz)/Length of Waveform } N \times \text{divider } M$$

Having a higher N value or divider M increases the fidelity and stability of the current outputs at the cost of max SinDAC frequency, while having a lower clock speed directly reduces the maximum SinDAC frequency. Generally, there are only a few (10+) discrete speeds at which the SinDAC can operate in this design, but a few hundred Hz difference may reduce the noise faster than the signal in such a way as to improve the SNR substantially, leading to improvement.

In one embodiment, a change of about 800 Hz in the SinDAC frequency over 6 steps was created, by setting the rate of the SinDAC using the ADC interrupt frequency. Given an 80 MHz clock rate, and an N=32 point sine wave with an M=125 divider, sufficiently clean signals are produced at a SinDAC frequency of 20 kHz. Changing the divider M changes both the ADC sampling rate and the output of the N=32 point sine wave, synchronizing both the SinDAC current and the sampling of the returning voltage. These outputs would be well within the roll-off of a band-pass filter used to precondition the returning voltage signal, allowing a potential increase in Signal to Noise Ratio.

Dynamic noise-filtering with dynamic SinDAC frequency—One way to remove the limitations of only a few discrete speeds of SinDAC is to change the filtering technique on the voltage inputs by using a mixed-signal design switched-capacitor filter network with a high Q (ideally 4-8, given a chip like the Maxim 7491).

Improving SNR while sacrificing signal bandwidth—One way to improve SNR is to collect and process a buffer of data with a longer time interval. For example, if the buffer length is 2 ms, then volume versus time can be measured at 500 Hz. However, if the buffer length is increased to 20 ms, volume versus time is measured at 50 Hz, but SNR is greatly improved.

Figure 12:
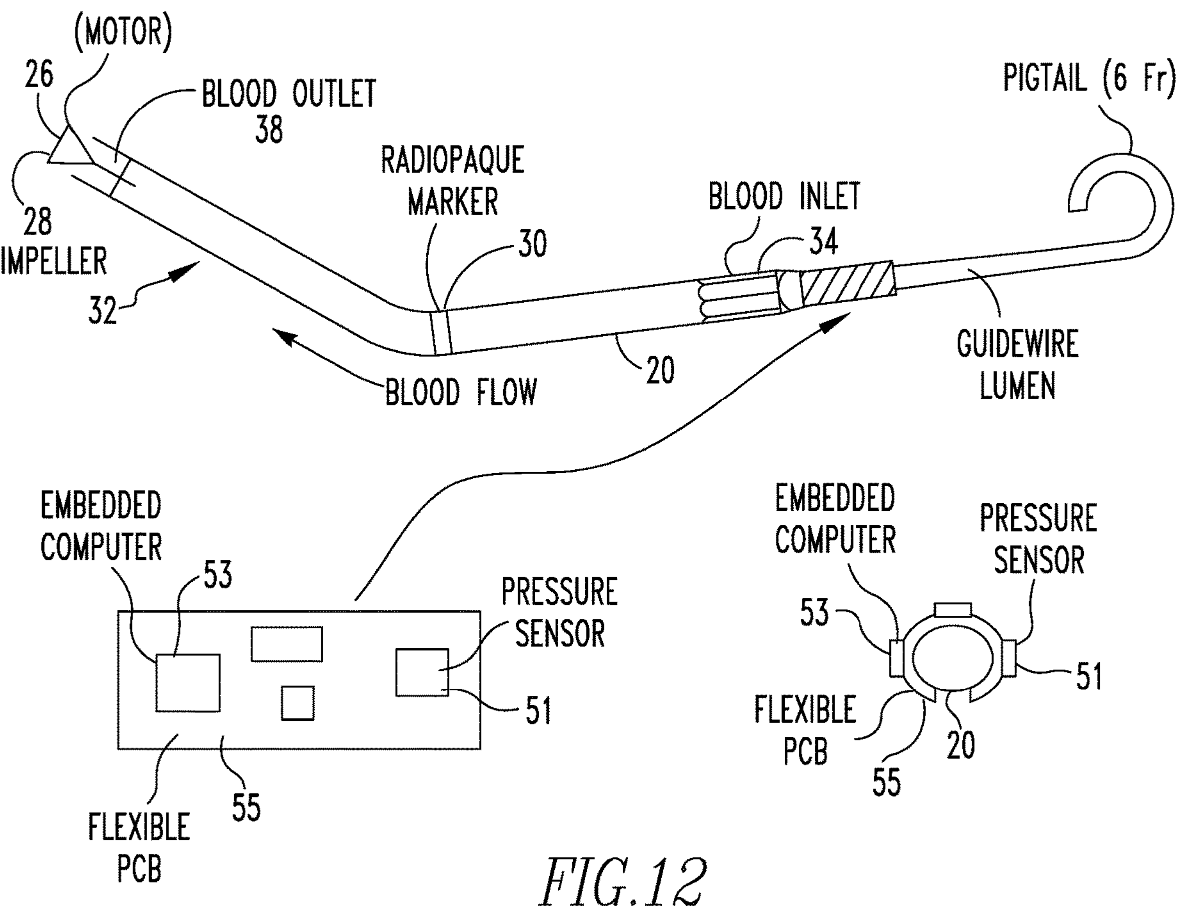
FIG. 12 shows a flexible printed circuit board wrapped around the catheter.
Figure 13:
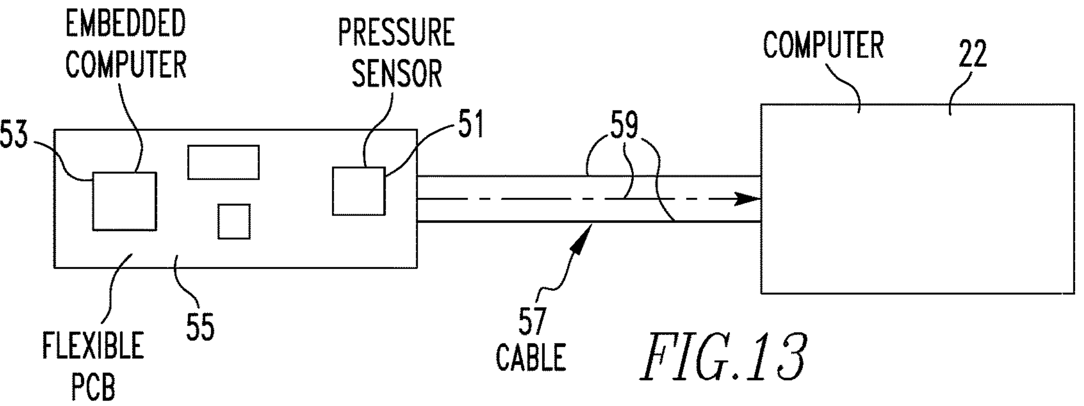
FIG. 13 shows the embedded system is interfaced to the main computer with a cable.

Left ventricular pressure—To improve clinical usefulness of the invention it is possible to include a pressure sensor 51 within the left ventricle. The challenge is not necessarily the size of the transducer, but the cost of routing three additional wires along the cardiac assist device 14. One solution to the device 14 diameter is to embed an embedded computer 53 along with the pressure sensor 51 distal to the inlet port 34 of the cardiac assist device 14. FIG. 12 shows a flexible printed circuit board 55 wrapped around the shaft 20. The printed circuit board 55 has the embedded compute 53 and the pressure sensor 51. FIG. 13 shows the embedded computer 53 and pressure sensor 51 is interfaced to the main computer 22 with a cable 57 having 3 or more wires. In this configuration only 3 wires are necessary to implement both admittance-derived volume and left ventricular pressure. One wire is voltage supply, one wire is ground, and the third wire is serial output. The serial output encodes the raw measurements, which will then be processed in the usual way on the main computer 22. In this configuration the admittance circuitry (sinDAC, and ADC) is included on the flexible PCB wrapped around the tip of the pump.

Clinical Use Cases: General—The ability of MCS 32 devices to maintain peripheral perfusion while mechanically unloading the heart 12 has the potential to improve mortality across at least three large groups of patients (7): 1. high risk percutaneous coronary intervention (PCI), 2. acute myocardial infarction (MI) with or without cardiogenic shock, and 3. acute decompensated heart 12 failure.

While the first category of high-risk PCI is an elective surgery and is typically performed over a surgical (short) period, for the last two categories, MCS 32 devices are implanted for up to 6 days as a bridge-to-recovery or bridge-to-decision for a more long-term ventricular assist implant. In these patients, indwelling time is longer, and bridging to recovery is not guaranteed.

Goals of hemodynamic support—The overarching goal of hemodynamic support is to maximize function by increasing both Cardiac Output (CO, the MCS 32 control point), and Mean Arterial Pressure (MAP, optimized by medication). The product is the Cardiac Power Output (CPO=total CO*MAP) and low CPO is now well accepted as the single most important correlate of mortality in cardiogenic shock. Studies have also shown that the goal of keeping the CPO≥~0.6 W with MCS 32 devices is predictive of decreasing heart failure at 30 days. While the measurement of pressure is currently integrated into many MCS 32 devices (e.g., the Impella device has an integrated pressure sensor 16, used for device placement), the only control point for an MCS 32 device is the motor 26 speed, which increases CO with increasing motor 26 speed (flow). In practice, this translates to a clinical support goal of setting the MCS 32 device flow as high as possible without the causing suction due to high pump speeds (where the motor 26 is spinning, but no blood is moving through the MCS 32). The positive impact of an MCS 32 device is highly dependent on the flow rate of the pump, which can be adjusted in the majority of pumps, but the initial flow rate is rarely changed during recovery.

The key indicator of patient stability is Total Cardiac Output (total CO), which is the summation of the pump CO (the amount of blood in Liters ejected by the pump per min), and the native CO (The amount of blood in Liters ejected by the heart per min). Total CO=pump CO+native CO. Native CO is dependent on patient health, while pump CO is controlled by the operator of the MCS 32 device, and estimated using the current draw on the motor 26, or measured RPM, or in some cases, by a flow measurement integral to the pump that is either EM, acoustic, or pressure differential based.

Clinical Use Case 1: Native CO to inform start of weaning from MCS 32—MCS 32 device implantation is not without risk, and longer indwelling times can lead to infectious complications in the form of local infections, bacteremia, and sepsis. Patients who suffer from these complications face a substantially longer hospital stay. Removal of the MCS 32 device requires "weaning" the patient from pump support by slowly (over hours) reducing pump speeds and closely monitoring hemodynamics to ensure that the heart 12 does not decompensate from lack of support. The decision to begin weaning the patient from the MCS 32 device relies heavily on a subjective clinical assessment of the patient (instead of an objective measurement of CPO, impossible without native CO). In some research institutions, CPO is estimated directly using pressure measurement, and transthoracic echocardiography to look at native CO (Ejection Fraction) during the hours long weaning process, but this requires the resources of a surgeon, a heart failure cardiologist, and an expert cardiologist experienced in echocardiographic parameters. This is a huge amount of resources if the weaning process takes a long time, or if recovery is not actually complete. One potential clinical use of measuring Native CO using the Abiomed Impella device, is that it can provide a real-time assessment of patient condition.

Clinical Use 2: Native CO for automatic weaning control input—Weaning a patient from an implanted MCS 32 device need not be a manual process. Native CO can be measured in real time using the invention described alongside pump flow to provide insight into the slowly improving condition of a patient supported by MCS 32. Weaning would happen in this way optimally, allowing for total CO to remain constant, while the patient's heart 12 recovers on its own. A number of well known-control algorithms could be applied automatically to the pump flow control based on the patient's measured, Native CO.

Clinical Use 3: If pressure is available, then the device is capable of measuring native pressure volume loops. Pressure-volume loops provide valuable information about the hemodynamic status of the heart.

Embodiment 1: Used in Preliminary Studies

Electrodes 18 used: The electrodes 18 used in this embodiment were purchased in two sizes, to accommodate the two different catheter body sizes, from Johnson Matthey, UK. Two were used as electrodes 1 and 2 (with a smaller diameter), and two were used as electrodes 3 and 4 (with a larger diameter). The final embodiment is the bottom electrode configuration.

Electrode Spacing: Electrode spacing was chosen to maximize the span of the chamber of interest (the left ventricle) while ensuring that all four electrodes 18 would stay below the valve (and therefore in the chamber of interest). This was done by making sure that the most proximal electrode (electrode 4) is close to the radiopaque marker 30 that surgeons use to place the pump inlet inside the LV, and the pump outlet outside the LV (in the aorta). By co-locating electrodes 3 and 4 with the radiopaque marker 30, it is ensured that the electrodes 18 will be within the LV if the pump is functioning correctly.

Electrode Wiring 24: Wiring 24 considerations for the preliminary studies embodiment required us to keep the wiring 24 on the outside of the lumen for the distal electrodes 1 and 2. This was done to keep the lumen free and clear for use by a guidewire to implant the catheter. The wiring 24 on the proximal electrodes 3 and 4 is run internal to the catheter body to avoid changing their large surface area, and the wiring 24 on the distal electrodes 1 and 2 was run outside of the catheter with minimal contact area (see FIGS. 3, 6, 9 and 10). The key consideration for the diameter (or gauge) of the wire is that they should be as thin as possible. If wiring 24 is run internal to the lumen between the pump inlet and outlet, the requirement to be thin is to reduce impediment of blood flow or required guidewires for implant. If wiring 24 is run external to the pump, then the wiring 24 is required to be thin to reduce the size of the sheath necessary to implant (allowing for an easier surgical technique).

Figure 11:
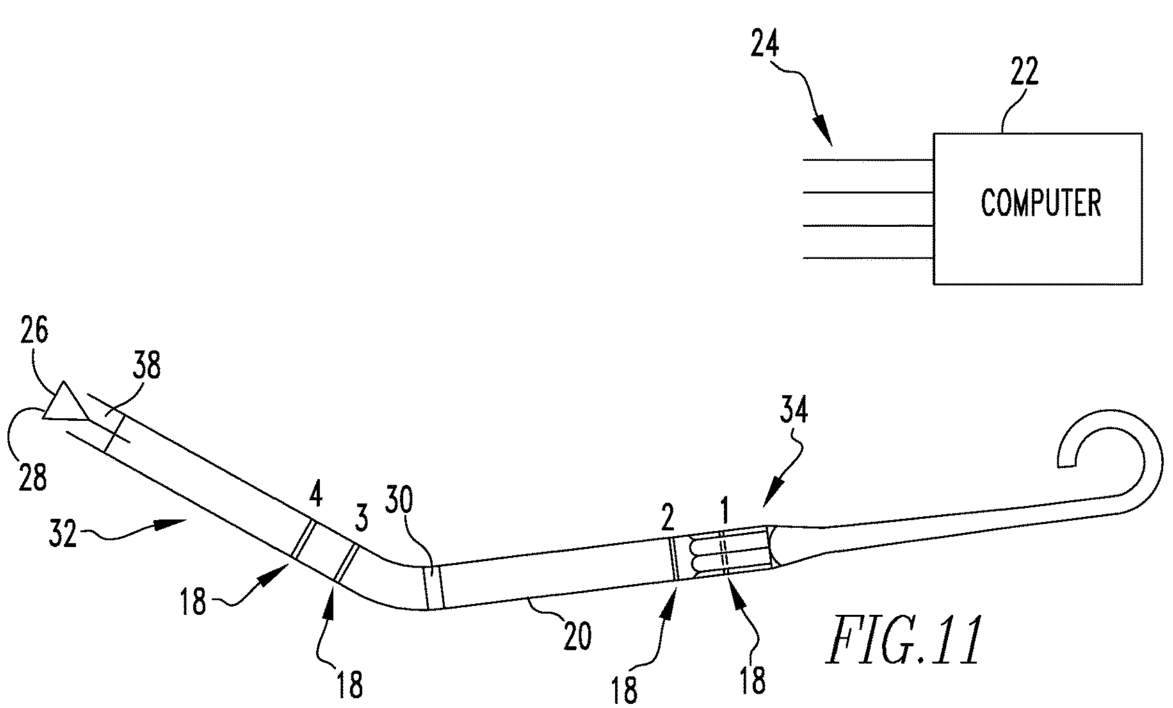
FIG. 11 shows the claimed invention with alternative placement of the electrodes.

In another embodiment, as shown in FIG. 11, the wiring 24 runs internal to the plastic body (but not in the lumen space). This will be similar in function to the way that nitinol is embedded in the catheter body itself for the purpose of making the Impella catheter stiffer. A tradeoff in volume sensitivity to allow the electrodes 18 to be placed closer together will also be exploited.

Motor 26 noise quantification: Fourier frequency analysis of the motor 26 noise signal during pump operation was used to determine the optimal frequencies to use for the cardiac volume measurements. It was determined that the pump noise was at 50 khz, and at 100 kHz at all 9 pump speeds for an Abiomed Impella device (Danvers, MA), and did not overlap with the measurement. It was found from FIG. 7 that any frequency at least 5 kHz away from DC, and not an integer multiple of 50 kHz could be utilized for the admittance-based volume measurement. 20 kHz was chosen. In a fictitious example where 30 kHz was where motor 26 noise was detected, any frequency from 10 kHz to 25 kHz, or from 35 kHz to 100 kHz, for example, can be chosen. FIG. 7 is a Fourier analysis of motor 26 electromagnetic noise vs. admittance signal for all 9 motor 26 speeds (P1-P9). Note that the signal is 40 dB higher than the surrounding noise floor (60 dB), meeting our success. Motor 26 noise Quantification. Signal is at 20 kHz, note peaks at 50 and 100 kHz representing motor 26 noise. Each color is a different pump speed.

Works Cited, all of which are incorporated by reference, herein.

[1] D. E. Haines et al., "Validation of a defibrillation lead ventricular volume measurement compared to three-dimensional echocardiography," Heart Rhythm, June 2017.

[2] L. M. Holt, M. L. Oglesby, A. P. Wang, J. W. Valvano, and M. D. Feldman, "A Real-Time Hemodynamic ICD Measurement: Evaluation in Chronically Implanted Canines With Pacing-Induced Dilated Cardiomyopathy," J Am Coll Cardiol EP, vol. 5, no. 6, pp. 742-743, June 2019 PMID: 31221363.

[3] E. R. Larson, M. D. Feldman, J. W. Valvano, and J. A. Pearce, "Analysis of the Spatial Sensitivity of Conductance/Admittance Catheter Ventricular Volume Estimation," IEEE Trans. Biomed. Eng., vol. 60, no. 8, pp. 2316-2324, August 2013.

[4] K. Raghavan et al., "Electrical Conductivity and Permittivity of Murine Myocardium," IEEE Trans. Biomed. Eng., vol. 56, no. 8, pp. 2044-2053, August 2009.

U.S. Patents and application 10,420,952

10,376,177

10,076,669

9,820,673

9,295,404

7,925,335

6,494,832

20110152661

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. A method for assisting a heart of a patient comprising the steps of:

producing a source signal having electrical currents having a frequency by a sensor implanted in the patient, the sensor in communication with a cardiac assist device implanted into the patient to assist the heart with pumping blood and the heart, the cardiac assist device has a shaft that is adapted to be engaged with the heart, the cardiac assist device includes a motor and an impeller disposed in the shaft which is driven by the motor to assist the heart with pumping blood, thereby reducing mechanical load on the heart and promoting recovery, the sensor includes a computer for data acquisition and analysis of the source signal, the computer in communication with the electrodes, the computer produces the source signal which includes the electrical currents having the frequency and measures corresponding voltages to make measurements and analyze the measurements and noise from the motor associated with the measurements to make real-time volume measurements of the heart, the sensor dynamically shifting the frequency of the electrical currents of the source signal to avoid noise from the motor in the patient during operation of the cardiac assist device while the cardiac assist device is implanted in the patient;

monitoring the heart and noise from the motor in the patient by the sensor with the source signal; and the sensor dynamically shifting the frequency of the electrical currents of the source signal in real time to avoid the noise from the motor in the patient during operation of the cardiac assist device while the cardiac assist device is implanted in the patient.

2. The method of claim 1 including the steps of the pump drawing blood from a left ventricle of the heart through an inlet port of the shaft and expelling blood into an ascending aorta of the heart through an outlet port of the shaft.

3. The method of claim 2 wherein the sensor includes electrodes in communication with the computer and including the step of emitting the source signal from the electrodes, the electrodes are in direct contact with the shaft that is positioned in the heart.

4. The method of claim 3 including the step of the computer making admittance-based measurements from the source signal and analyzing the admittance based measurements and noise from the motor associated with the admittance-based measurements to make real-time admittance-based volume measurements of the heart.

5. The method of claim 4 including the step of the computer making admittance-based measurements and analyzing the admittance-based measurements and noise from the motor associated with the admittance-based measurements to make real-time admittance-based volume measurements of the heart using a Fast-Fourier Transform in real time.

6. An apparatus for a heart of a patient comprising:

a cardiac assist device adapted to be implanted into the patient to assist the heart with pumping blood, the cardiac assist device has a shaft that is adapted to be engaged with the heart, the cardiac assist device includes a pump having a motor and an impeller engaged with the shaft which is driven by the motor to assist the heart with pumping blood, thereby reducing mechanical load on the heart and promoting recovery; and a sensor adapted to be implanted into the patient, the sensor having a computer, the computer produces a source signal, the sensor in communication with the cardiac assist device and the heart, the sensor adapted to monitor the heart with the source signal, the computer performing data acquisition and analysis of the source signal, the source signal includes electrical currents having a frequency, the computer measures corresponding voltages to make real-time volume measurements of the heart, the sensor dynamically shifting the frequency of the electrical currents of the source signal to avoid noise in the patient from the pump during operation of the cardiac assist device while the cardiac assist device is implanted in the patient, and a microcontroller clock or oscillator that is at a frequency at least 100× higher than the electrical currents at the frequency.

7. A method for assisting a heart of a patient comprising the steps of:

producing a source signal having electrical currents having a frequency by a computer of a sensor implanted in the patient, the sensor in communication with a cardiac assist device implanted into the patient to assist the heart with pumping blood and the heart, the cardiac assist device has a shaft that is adapted to be engaged with the heart, the cardiac assist device includes a pump having a motor and an impeller engaged with the shaft which is driven by the motor to assist the heart with pumping blood, thereby reducing mechanical load on the heart and promoting recovery, the computer performing data acquisition and analysis of the source signal, the computer measures corresponding voltages to make measurements and analyze the measurements to make real-time volume measurements of the heart, the sensor dynamically shifting the frequency of the electrical currents of the source signal to avoid noise in the patient from the pump during operation of the cardiac assist device while the cardiac assist device is implanted in the patient, and a microcontroller clock or oscillator that is at the frequency at least 100× higher than the electrical currents at the frequency;

monitoring the heart by the sensor with the source signal; and the sensor dynamically shifting the frequency of the electrical currents of the source signal in real time to avoid noise in the patient from the pump.

* * * * *